(12) United States Patent
Claypool et al.

(10) Patent No.: US 8,330,959 B2
(45) Date of Patent: Dec. 11, 2012

(54) MULTI-CHANNEL SURFACE PLASMON RESONANCE INSTRUMENT

(76) Inventors: Christopher L. Claypool, Carlsbad, CA (US); Emad S. Zawaideh, Carlsbad, CA (US)

( * ) Notice: Subject to any disclaimer, the term of this patent is extended or adjusted under 35 U.S.C. 154(b) by 208 days.

(21) Appl. No.: 12/729,506

(22) Filed: Mar. 23, 2010

(65) Prior Publication Data
US 2010/0238443 A1 Sep. 23, 2010

Related U.S. Application Data

(60) Provisional application No. 61/162,564, filed on Mar. 23, 2009.

(51) Int. Cl.
*G01N 21/55* (2006.01)
(52) U.S. Cl. .................. 356/445; 422/85.11; 422/82.05; 435/287.5
(58) Field of Classification Search .......... 356/445–448, 356/301, 369; 422/82.01–82.12; 385/12, 385/129; 435/287.2
See application file for complete search history.

(56) References Cited

U.S. PATENT DOCUMENTS

| | | | | |
|---|---|---|---|---|
| 5,485,277 A | * | 1/1996 | Foster | 356/445 |
| 5,822,073 A | * | 10/1998 | Yee et al. | 356/445 |
| 8,216,518 B2 | * | 7/2012 | Chau et al. | 422/82.11 |
| 2007/0030489 A1 | * | 2/2007 | Salamon et al. | 356/451 |
| 2007/0291262 A1 | * | 12/2007 | Candiloro | 356/244 |
| 2010/0267163 A1 | * | 10/2010 | Ran et al. | 436/164 |

* cited by examiner

*Primary Examiner* — Hoa Pham
(74) *Attorney, Agent, or Firm* — John R. Ross; John R. Ross, III

(57) ABSTRACT

A robust multichannel SPR instrument with exceptionally high sensitivity (<pg/mm$^2$). The instrument utilizes an SPR detection scheme providing multiple reflections from a planar light guide configuration to amplify the reflected light intensity changes near the resonance angle. This SPR approach is amenable to simultaneous multichannel detection while maintaining high sensitivity with a simple, cost-effective design. The idea of using multiple reflections to excite multiple surface plasmon waves seems counterintuitive at first because the SPR resonance will be broadened; the broadened resonance will diminish sensitivity for angle or wavelength detection modes. However, changes in reflected light intensity near the resonance angle will be amplified by the multiple reflections, thereby increasing the sensitivity of SPR utilizing intensity detection at a fixed angle of incidence.

20 Claims, 5 Drawing Sheets

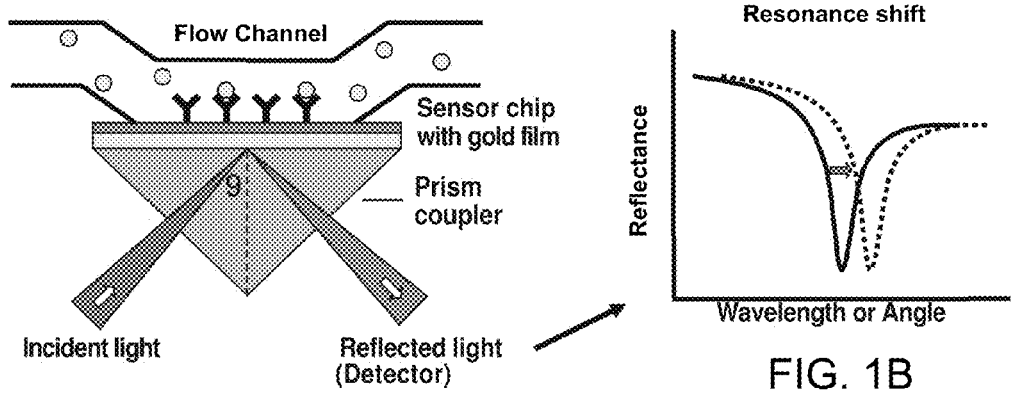
FIG. 1A
FIG. 1B
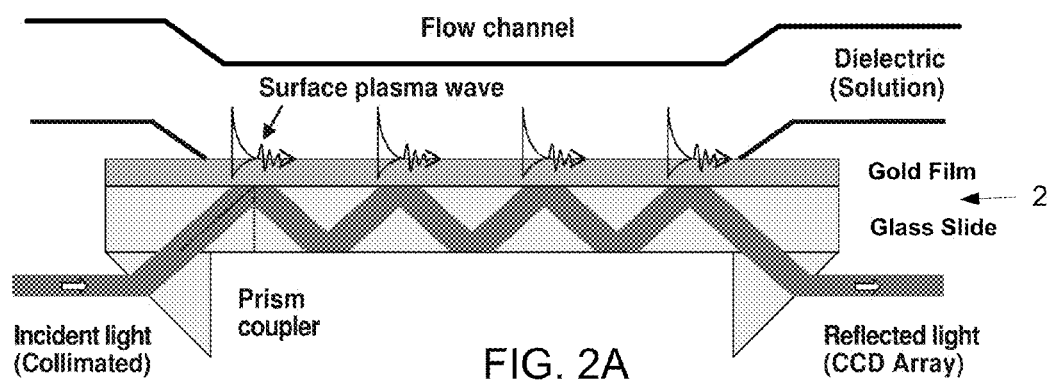
FIG. 2A
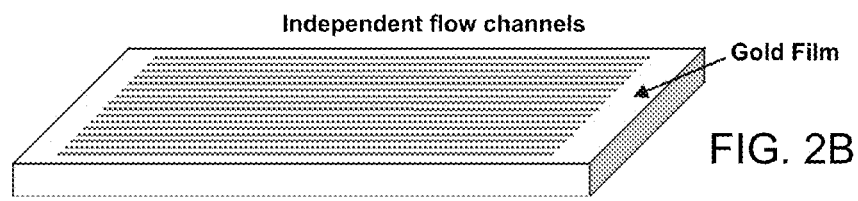
FIG. 2B

MULTI-CHANNEL SURFACE PLASMON RESONANCE INSTRUMENT

CROSS REFERENCE TO RELATED APPLICATIONS

This application claims the benefit of provisional application Ser. No. 61/162,564 filed Mar. 23, 2009.

FIELD OF THE INVENTION

The present invention relates to bio-molecular instruments and in particular to surface plasmon resonance spectroscopic instruments.

BACKGROUND OF THE INVENTION

Surface plasmon resonance (SPR) spectroscopy is a key enabling technology in the analysis of molecular interactions, an area of increasing importance for scientists in the academic, pharmaceutical, and biotechnology markets. SPR based analytical instruments provide real-time specificity, affinity, and kinetics information of biomolecular interactions without requiring flourophore labeling. These data give insights into protein functionality, elucidate disease mechanisms, and play a key role in the drug discovery process. SPR can monitor interactions between proteins and immobilized ligands in real time to provide specificity, affinity, and kinetics information. These data give insights into protein functionality, elucidate disease mechanisms, and play a key role in the critical decisions needed for the efficient development and production of therapeutics. SPR instruments are used by scientists in the academic, pharmaceutical, and biotechnology sectors in key application areas such as antibody characterization, proteomics, immunogenicity, lead characterization, and biopharmaceutical development and production.

Although several commercial SPR instruments are currently available, their basic designs do not differ significantly from the original concept described 25 years ago. Commercially available SPR instruments have been limited in their application to high throughput screening and proteomics analysis by the low number of channels that can be detected simultaneously. Providing robust multichannel SPR instrumentation with high sensitivity is a key challenge in the continued development of SPR spectroscopy. Multichannel SPR instrumentation with high sensitivity is needed for direct detection in high throughput screening in the search for new pharmaceuticals. Current SPR detection limits can be insufficient for the direct detection of low concentrations of small molecules, particularly those with low binding affinities. The overall value and utility of SPR spectroscopy would be greatly increased in the drug discovery process, in particular for small molecule research, with the development of commercial SPR instrumentation with multichannel performance and high sensitivity. The analysis of biomolecular interactions is an integral part of the drug discovery process, and many millions of dollars are spent early in drug development on screening compounds for receptor binding.

SPR spectroscopy has been commercialized by several companies and has become a competitive technology in the field of direct, real time observation of protein interactions. Biacore, a major provider of SPR systems, was purchased in 2006 by GE Healthcare for $390 million. The global market for protein interaction analytical systems and consumables is estimated to be $650 million.

SPR spectroscopy is an optical technique that detects changes in the refractive index in the immediate vicinity of a thin film of metal deposited on a glass substrate. The surface plasmon resonance is observed as a dip in the intensity of the reflected light from a metal film, typically gold or silver, that is in contact with a dielectric (solution). The angle of minimum intensity of reflected light, the resonance angle, is affected by changes in the refractive index of the medium near the surface of the metal film. Binding of molecules in solution to surface immobilized receptors alters the refractive index of the medium near the metal surface. By tracking the wavelength, incident angle, or intensity of the reflected light near the resonance angle, changes in the refractive index near the metal film (~100-500 nm) can be monitored in real time to accurately measure the amount of bound analyte, its affinity for the receptor, and the association and dissociation kinetics of the interaction.

Much research effort has been focused on the development of multichannel SPR instrumentation. Multichannel detection is particularly significant for high throughput screening applications such as drug discovery and proteomics research where many thousands of ligand-receptor or protein-protein interactions must be rapidly examined. The simultaneous measurement of multiple channels has the technical advantage of allowing designated in situ reference channels that can be used to normalize for instrument errors arising from sensor inhomogeneity, uneven sample introduction, and temperature variation. Additionally, multichannel detection allows for dedicated control channels that can be used to probe signal shifts using repeated standards to improve the quality of the binding data. The current state of the art is a four-channel system based on angular interrogation made by Biacore. A significant obstacle to multichannel SPR systems is that SPR angle or wavelength detection modes are cumbersome to implement in large arrays due to the optical complexity of the instrumentation. As a result, researchers have recently focused on SPR imaging approaches because the spatial resolution afforded from imaging with a 2D detector array can be combined with patterned microarrays of biomolecules to allow for high throughput analyses. However, it is often difficult to maintain sensitivity when using SPR designs based on intensity detection.

Commercial SPR instruments are generally capable of resolving a change of refractive index within about $1 \times 10^{-5}$ to $1 \times 10^{-6}$, which corresponds to a mass sensitivity of ~1 $pg/mm^2$ of absorbed analytes, depending on the surface functionalization chemistry. This sensitivity can be insufficient for the direct detection of low concentrations of small molecules, particularly those with low binding affinities. For example, in direct immunoassays, antibodies are immobilized on the sensor surface and subjected to the binding interaction of the analyte of interest. The change in resonance angle due to the binding interaction between the analyte and the antibody is directly proportional to the concentration of bound analyte. Although straightforward to perform, direct methods are often only useful for large molecules because small molecules have insufficient mass to effect a measureable change in the refractive index. As a result, many direct immunoassay experiments involving the detection of small molecular analytes are based on fluorescence detection using labeled analytes. Although alternative assay methods such as indirect competitive inhibition can be used to enhance small molecule detection, direct detection assays are often desirable due to their simplicity. The overall value and utility of SPR spectroscopy would be greatly increased in the drug discovery process, in particular for small molecule research, with the development of commercial SPR instrumentation with multichannel performance and high sensitivity. Most traditional SPR measurements are based on the Kretschmann configuration where a prism is used to couple the light into the metal film. The surface plasmon resonance occurs when the external light energy resonantly induces the free electrons of the metal to oscillate at the metal-dielectric interface. As a result, the radiant energy is absorbed by the metal at a certain incident angle, and the resonance coupling is observed as a sharp dip in the reflected light spectrum whose angular position is extremely sensitive to the index of refraction of the dielectric medium in contact with the metal surface. Previous work to enhance SPR sensitivity has focused on narrowing the SPR resonance to increase resolution in either wavelength or angle detection modes. This has been accomplished through a variety of designs where multilayer dielectric structures are deposited on either side of the SPR active metal film. These approaches have led to sensitivity enhancements as much as seven times that of conventional SPR sensors. Similar sensitivity improvements have been made for intensity detection modes by enhancing the SPR image contrast with dark field methods and polarization contrast methods. These techniques have shown sensitivity to changes in refractive index of $2 \times 10^{-6}$. The challenge lies in maintaining these high sensitivities with a multichannel instrument.

The Need

What is needed is a robust multichannel SPR instrument with exceptionally high sensitivity permitting analysis of small molecules with low binding affinities.

SUMMARY OF THE INVENTION

The present invention provides a robust multichannel SPR instrument with exceptionally high sensitivity ($<pg/mm^2$). The instrument utilizes an SPR detection scheme providing multiple reflections from a planar light guide configuration to amplify the reflected light intensity changes near the resonance angle. This SPR approach is amenable to simultaneous multichannel detection while maintaining high sensitivity with a simple, cost-effective design. The idea of using multiple reflections to excite multiple surface plasmon waves seems counterintuitive at first because the SPR resonance will be broadened; the broadened resonance will diminish sensitivity for angle or wavelength detection modes. However, changes in reflected light intensity near the resonance angle will be amplified by the multiple reflections, thereby increasing the sensitivity of SPR utilizing intensity detection at a fixed angle of incidence.

Instruments of the present invention include a planar light guide defining a first side and a second side and having a thin metal film deposited on said first side, a first light coupler and a second light coupler adapted to couple light into and out of said planer light guide so as to produce multiple reflections between the first and second sides of said planer light guide, a light source for illuminating said planer light guide, a flow cell adapted to flow bio-molecular fluid samples across said first side of said planer light guide, an optical detector adapted to monitor light exiting said planer light guide and a computer processor programmed to analyze information provided by the optical detector to determine bio-molecular interactions without requiring flourophore labeling.

BRIEF DESCRIPTION OF THE DRAWINGS

FIGS. 1A and 1B describe a prior art SPR technique.
FIGS. 2A and 2B describe features of preferred embodiments of the present invention.

DETAILED DESCRIPTION OF PREFERRED EMBODIMENTS

Figure 3:
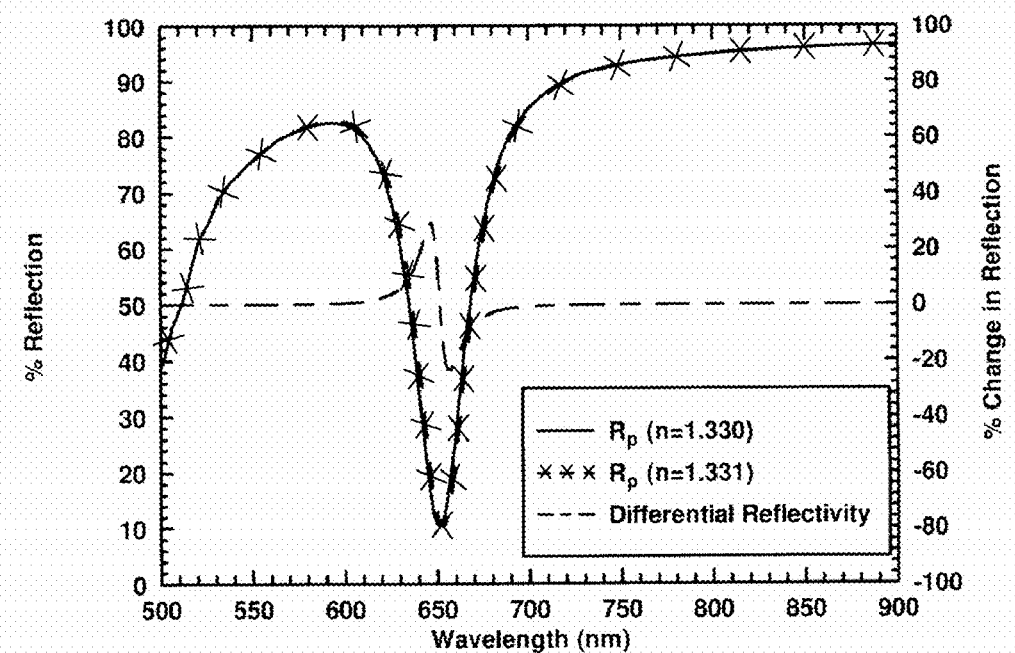
FIG. 3 shows calculated results for a typical prior art SPR experiment.

A preferred embodiment of the present invention is a 50 channel SPR instrument with an order of magnitude higher sensitivity than currently available SPR instrumentation. This instrument utilizes a novel SPR detection scheme providing multiple reflections from a planar light guide configuration to amplify changes in the reflected light intensity near the resonance angle. This SPR approach is amenable to simultaneous multichannel detection while maintaining high sensitivity with a simple, cost-effective design. The system includes an optoelectronic system for the excitation and detection of the surface plasmon resonance utilizing the novel planar light guide configuration. Three important components include: (1) a multichannel microfluidic system for sample handling, (2) chemical modification of the sensor surface for the attachment of biomolecular recognition elements, and (3) data analysis software. Important features of the present invention are illustrated in FIGS. 2A and 2B. With the appropriate optics, a collimated beam can be made to illuminate a large region of a glass slide as shown in FIG. 2A. Using poly (dimethylsiloxane) (PDMS) microfluidic technology a flow cell made of many independent, parallel flow channels is fabricated along the length of the disposable glass slide. (Details of this PDMS technology are well described in the literature. For example see: McDonald, J. C.; Duffy, D. C.; Anderson, J. R.; Chiu, D. T.; Wu, H.; Schueller, O. J. A.; Whitesides, G. M. Fabrication of microfluidic systems in poly(dimethylsiloxane). *Electrophoresis* 21, 27, (2000); Wheeler, A. R.; Chah, S.; Whelan, R. J.; Zare, R. N. Poly (dimethylsiloxane) microfluidic flow cells for surface plasmon resonance spectroscopy. *Sens. Actuators B* 98, 208, (2004); Fiorini, G. S.; Chiu, D. T. Disposable microfluidic devices: fabrication, function, and application. *BioTechniques* 38, 429, (2005); Whitesides, G. M. The origins and the future of microfluidics. *Nature* 442, 368, (2006); Yager, P.; Edwards, T.; Fu, E.; Helton, K; Nelson, K.; Tam, M. R.; Weigl, B. H. Microfluidic diagnostic technologies for global public health. *Nature* 442, 412, (2006); Karlsen, S. R.; Johnston, K. S.; Yee, S. S.; Jung, C. C. First-order surface plasmon resonance sensor system based on a planar light pipe. *Sens. Actuators B* 32, 137, (1996).)

By imaging the reflected light intensity with a CCD array, the SPR response of the independent, parallel flow channels can be monitored simultaneously. Assuming previously demonstrated microfluidic channel dimensions of 200 microns× 60 microns, 50 independent flow channels can be monitored on a high index glass slide with standard dimensions of 3 inches×1 inch×1 mm.

Previous work by Karlsen et al. (see above) demonstrated SPR with a planar light pipe configuration. In their study a planar light pipe was combined with an SPR active metal surface in order to monitor several angles of incident light simultaneously. The length of the SPR active metal layer was kept purposely short (<3 mm) in order to avoid multiple reflections from interacting with the metal layer. Rather than probing a single reflection at the metal surface with multiple input angles of light, Applicant's approach will monitor multiple reflections of the SPR active metal with a single incident angle of collimated light. Imaging the output light with a CCD array allows many independent, parallel flow channels to be simultaneously monitored, while the multiple reflections on the metal surface from a planar light guide configuration serve to amplify the changes in reflected light intensity near the resonance angle. In this way, an SPR instrument can be constructed with multichannel performance and sensitivity that is as high or higher than existing instrumentation.

Applicants' Modeling

Simulations of SPR reflectivity were generated with SCI's FilmWizard™ software, an optical thin film modeling package based on Abelès 2×2 matrix method (as described in Abelès, F. Research on the propagation of electromagnetic waves in stratified media application to thin films. *Ann. Phys.* 5, 596, (1950)). All simulations were performed with a gold film thickness of 65 nm, a prism and glass slide refractive index of 1.728, and an incident TM polarized light angle of 56.5 degrees. In SPR imaging, spatial differences in the reflected intensity resulting from changes in refractive index at the metal surface are measured at a fixed angle. Consider a bare gold surface in contact with water (refractive index=1.330). The theoretical SPR curve is shown in FIG. 3. Increasing the index of the solution by $1 \times 10^{-3}$ causes the SPR minimum to shift in wavelength. The percent change between these two curves is shown in the differential reflectivity curve (the dashed line in FIG. 3). In a typical SPR imaging experiment, the angle and incident wavelength would be chosen in order to maximize the intensity difference between the two curves. At the wavelength corresponding to the maximum differential reflectivity, an increase in index (binding of analytes) will cause an area to appear brighter.

Figure 4:
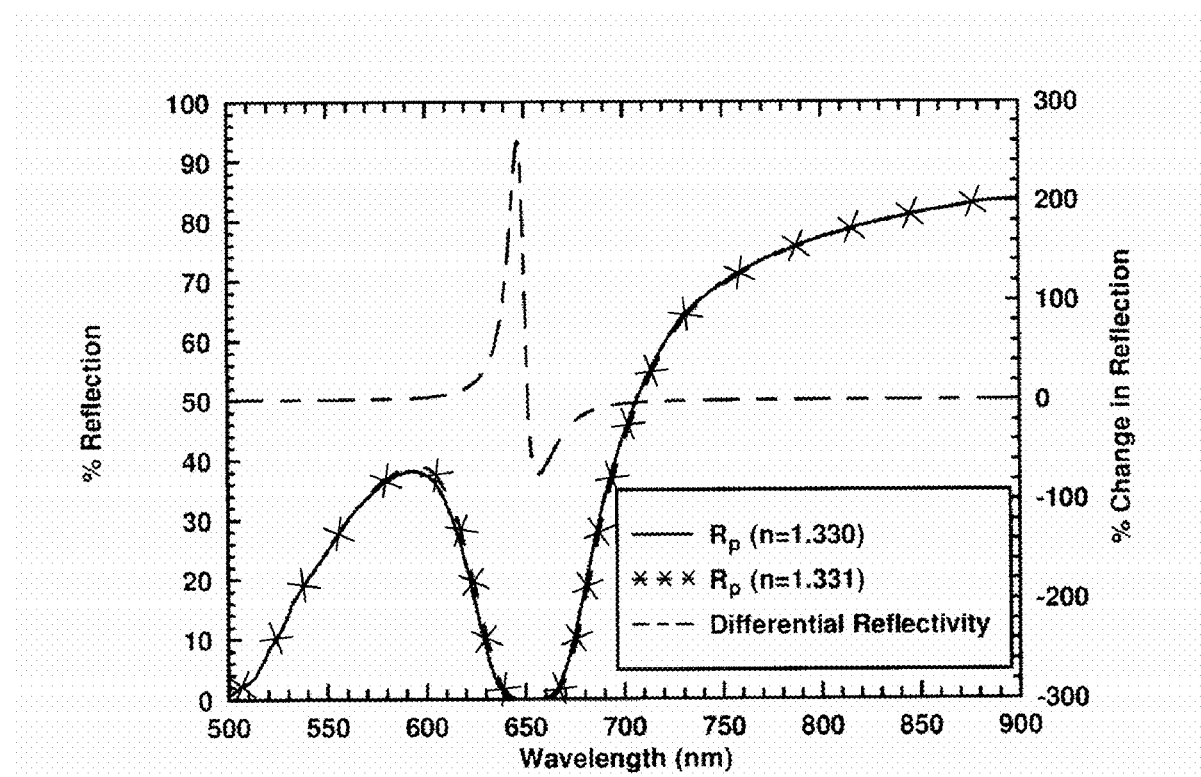
FIG. 4 shows calculated results for an SPR experiment utilizing embodiments of the present invention with five reflections of an illuminating light beam.

Consider now the same scenario with a planar light guide design and five reflections at the gold surface. The results are shown in FIG. 4. As might be expected, the SPR absorption from the multiple reflections is higher and the reflected intensity is much less. Additionally, both of the SPR curves are broadened. This resonance broadening would lower sensitivity if shifts in angle or wavelength were being monitored. However, the calculated differential reflectivity curve (% change in reflection) shows a substantial amplification in sensitivity for five reflections at the gold surface compared to the single reflection shown in FIG. 3.

Figure 5:
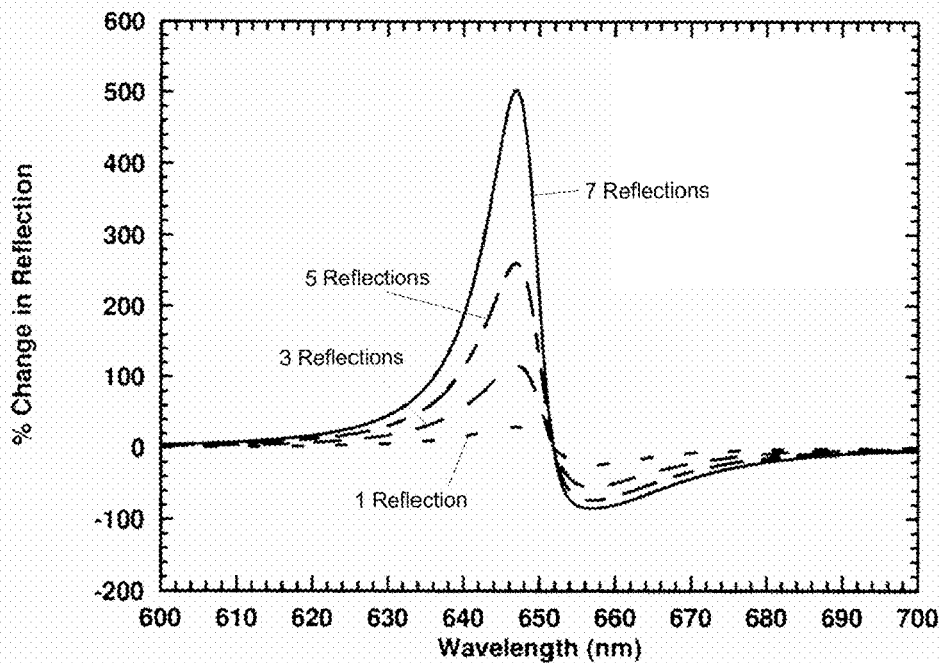
FIG. 5 shows calculated results utilizing embodiments of the present invention with 1, 3, 5, and 7 reflections.

Simulated differential reflectivity curves are shown for 1, 3, 5, and 7 reflections in FIG. 5. Each additional reflection amplifies the differential reflectivity near the resonance wavelength. A key limitation of the multiple reflection approach is that absorption at the resonant wavelength also increases for each successive reflection, and there is virtually no reflected light at the resonance wavelength (approximately 650 nm in this example) for seven reflections.

Figure 6:
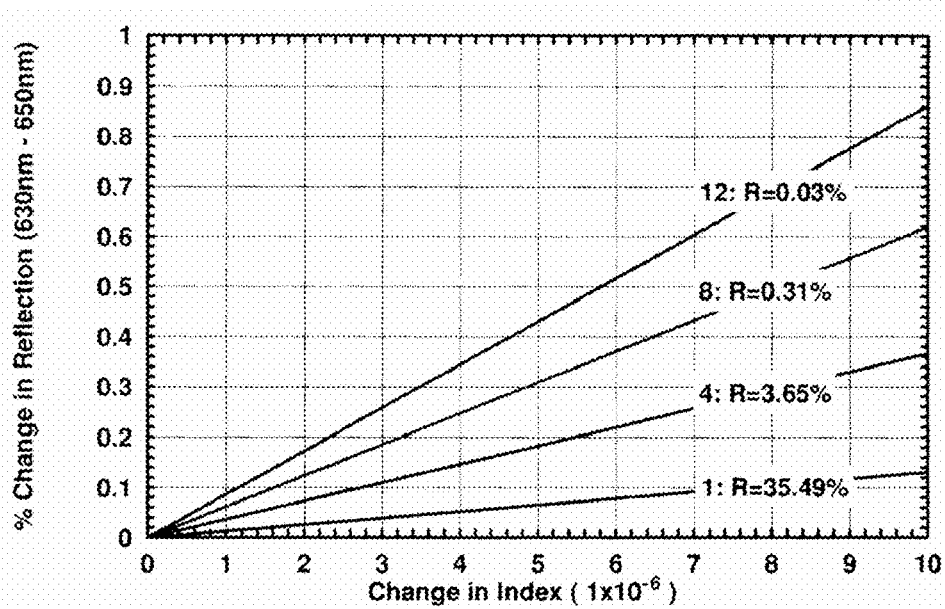
FIG. 6 shows calculated differential reflectivity over a wavelength range as a function of change of refractive index for 1, 4, 8 and 12 reflections.

However, consider an illumination source centered at 640 nm with a 20 nm wavelength spread that is near the resonance wavelength, such as a red LED. The calculated differential reflectivity of multiple reflections integrated over the wavelength range of 630 nm-650 nm versus change in solution index is shown in FIG. 6. The simulation shows that the integrated differential reflectivity increases with the number of reflections. As expected, the amount of absorbed light also increases with the number of reflections. With 8 reflections, most of the light is absorbed—only 0.31% is reflected. However, our experience has shown that this amount of reflection is easily measurable with the intensity of LED sources and sensitivity of modern detector arrays. In fact, with the proper design, detecting the reflected light from twelve reflections (0.03%) should be achievable. Assuming the CCD detector array can discern a 0.2% change in incident power, the proposed planar light guide configuration with 12 reflections will be sensitive to a change in refractive index of $2.5 \times 10^{-6}$.

Fifty Channel Instrument

Figure 7:
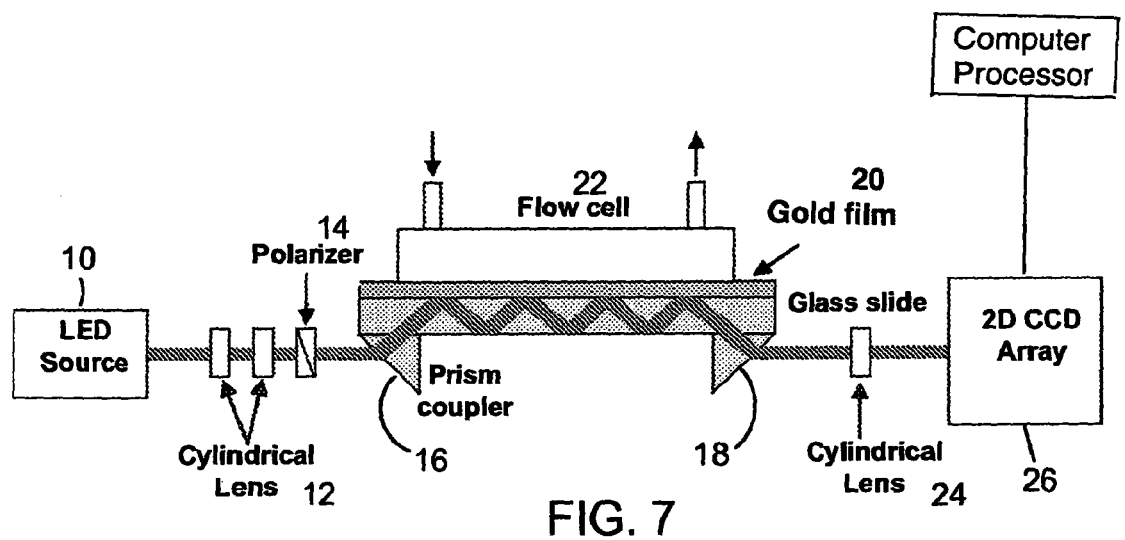
FIG. 7 is a schematic drawing showing important features of a preferred embodiment of the present invention.

A preferred embodiment of the present invention is a 50 channel SPR instrument with an order of magnitude higher sensitivity than currently available SPR instrumentation. A schematic of the system with the planar light guide configuration is shown in FIG. 7. Light from an LED source (or a linear array of LED sources) 10 is collimated using two cylindrical lenses 12 and passes through polarizer 14. The collimated and p-polarized beam is coupled into and out of the high index glass slide with two 45° high index prisms 16 and 18. A ~65 nm thick gold film 20 is deposited on the glass slide on top of which a liquid flow cell 22 is attached, so that solutions of interest can be easily introduced to the gold surface and switching between different solutions can be rapidly accomplished. The distance between the prisms can be adjusted to control the number of internal reflections in the glass slide. Translation stages (not shown) are used to adjust the angle of incidence of the input light impinging on the gold surface, since it may be necessary to adjust the incidence angle to maximize sensitivity for a given analyte/solution refractive index. The output light will be focused with a cylindrical lens 24 on a 2D CCD array 26, which will allow for pixel averaging to reduce noise.

Noise Characterization

An analysis of the noise level present in the SPR signal will place an upper limit on the resolution of the instrument. Three factors expected to contribute to the observed noise are detector noise, shot noise, and light source fluctuations. In order to reduce the effects of shot noise and detector dark noise, the light source should be intense enough to nearly saturate the detector. The attenuated reflection from multiple reflections may require a linear LED array in order to have a light source with enough intensity to maintain this condition. To experimentally measure the noise of the optoelectronic platform, an analysis of the reflectivity response of the sensor to a water sample will be monitored over time. For low levels of signal averaging, random shot noise should dominate and it is expected that averaging N detector scans or pixels should reduce noise inversely proportional to $N^{1/2}$. Increased averaging will reduce the relative significance of shot noise, and systematic noise components such as light source fluctuations and temperature variations should become dominate. A potential method of limiting these systematic contributions to noise is normalizing the reflectance data to a dedicated reference channel. Reflectance data will be collected and analyzed relative to a reference channel to determine the impact of this method for reducing the noise of the system. Based on these experiments, an optimal optoelectronic system configuration will be selected to best minimize noise.

Instrument Sensitivity

Calibration experiments will be performed to determine the sensitivity of the instrument to bulk refractive index variation. The sensitivity will be experimentally determined by performing a calibration of the device with a set of solutions with varying refractive index. This can be accomplished by measuring the change in reflectance as a function of concentration of sucrose solutions (water). The experimental sensitivity of the instrument is calculated by finding the slope of the calibration curve and multiplying by the maximum resolution of the device determined from the noise measurements. The expected change in reflectance as a function of index for the proposed design is shown in FIG. 6 for 1, 4, 8, and 12 internal reflections. The number of internal reflections will be experimentally varied by changing the distance between the input and output prisms and a comparison made between the theoretical and measured response curves. It is predicted that the proposed planar light guide configuration with 12 reflections will be sensitive to a change in refractive index of $2.5 \times 10^{-6}$.

A potential difficulty with this design is the low amount of reflected light expected from 12 reflections at the gold surface. This may increase noise to an unacceptable level depending on the intensity of the light source. A linear LED array may be required to increase input light intensity over the full width of the glass slide. Additional modification of the optical design (e.g., collimation strategy) may also be required in order to effectively measure the low amount of reflected light. An optimum optoelectronic design configuration should be determined that maximizes the amplification of the differential reflectivity from the multiple reflections while minimizing negative contributions to system noise.

Dynamic Range

A fundamental trade-off often exists between sensitivity and dynamic range when designing an SPR sensor. For most applications, high sensitivity over a narrow range of indices is more beneficial than moderate sensitivity over a large dynamic range. In the proposed SPR design, there are provisions to change the angle of incidence to accommodate a wide range of analyte/solution indices; however, in operation the reflected intensity will be monitored at a fixed incident angle. The dynamic range of the instrument needs to be large enough to observe a wide range of molecular binding events. Simulations indicate that the dynamic range of this design (at a fixed angle) will cover a refractive index range of $1 \times 10^{-2}$. This dynamic range should be sufficient since the index change associated with the adsorption of a monolayer of the protein bovine serum albumin onto the gold surface corresponds to a refractive index change of $\sim 2 \times 10^{-3}$. The dynamic range should be experimentally measured by the same method as the sensitivity; that is, the change in reflectance can be measured as a function of sucrose concentration in water. For small changes in index, it is predicted that the change in reflectivity is linear (FIG. 6). Most SPR designs choose to operate in this linear regime for ease of use. However, it may be possible to calibrate the response over a much wider dynamic range if the non-linearity is taken into account by modeling the expected response.

Variations

While there have been shown what are presently considered to be preferred embodiments of the present invention, it will be apparent to those skilled in the art that various changes and modifications can be made herein without departing from the scope and spirit of the invention. For example, in the above described embodiment the intensity of the reflected light is monitored near the SPR resonance after multiple reflections. The light intensity is resolved versus position on the glass slide by using a detector which could be a linear CCD array. In important potential variations, rather than limiting the detection method to a linear CCD array, we could include a two-dimensional CCD array in combination with a grating so that the reflected light intensity and wavelength could be resolved versus position after the multiple reflections. In this case the preferred light source is a white light source such as a tungsten halogen lamp. There are many other variation that are available that will be obvious to persons skilled in this art. Therefore, the scope of the patent should be determined by the appended claims and their legal equivalence and not by the examples that have been given.

What is claimed is:

1. A surface plasmon resonance instrument comprising:
    A) a planar light guide defining a first side and a second side and having a thin metal film deposited on said first side,
    B) a flow cell adapted to flow bio-molecular fluid samples across and in contact with said thin metal film on said first side of said planar light guide,
    C) a first light coupler and a second light coupler adapted to couple light into and out of said planar light guide so as to produce multiple surface plasmon resonance reflections between (i) the thin metal film in contact with the bio-molecular fluid samples on the first side and (ii) the second side of said planar light guide,
    D) a light source for illuminating said planar light guide,
    E) an optical detector adapted to monitor light exiting said planar light guide,
    F) a computer processor programmed to analyze information provided by the optical detector to determine bio-molecular interactions without requiring flourophore labeling,
wherein light intensity changes resulting from said multiple reflections are increased as compared to a single reflection.

2. The instrument as in claim 1 wherein said flow cell is a multi-channel flow cell.

3. The instrument as claim 2 wherein said multi-channel flow cell comprises at least 50 channels.

4. The instrument as in claim 1 wherein said light source is an LED light source.

5. The instrument as in claim 1 and further comprising a lens system adapted to collimate light from said light some.

6. The instrument as in claim 1 and further comprising a polarizer to polarize light from said light source.

7. The instrument as in claim 1 wherein said first and second light couplers are prism light couplers.

8. The instrument as in claim 1 wherein said planar light guide comprises a glass slide.

9. The instrument as in claim 1 wherein said glass slide is a microscope slide.

10. The instrument as in claim 1 and further comprising a lens adapted to produce images on said optical sensor.

11. The instrument as in claim 1 wherein said optical sensor is a CCD array.

12. The instrument as in claim 11 wherein said CCD array is a linear array.

13. The instrument as in claim 1 wherein said optical sensor is a two dimensional array.

14. The instrument as in claim 13 and further comprising a grating adapted to permit spectral analysis of light exiting said planar light guide.

15. The instrument as in claim 13 wherein said light source is a white light source.

16. The instrument as in claim 13 wherein said white light source is a tungsten halogen lamp.

17. The instrument as in claim 16 wherein the first and second light couplers are prisms.

18. The instrument as in claim 13 and further comprising a prism adapted to permit spectral analysis of light exiting said planar light guide.

19. The instrument as in claim 1 wherein the positions of the first and second light couplers are adjustable so as to vary the number of reflections from one reflection to a number of reflections greater than one.

20. The instrument as in claim 18 wherein the number greater than 1 is 12 or less than 12.

* * * * *